United States Patent [19]

Kolberg

[11] 4,132,644

[45] Jan. 2, 1979

[54] MEANS FOR REGULATING AND MONITORING DIALYSIS OF BLOOD IN A DIALYZER

[75] Inventor: Ole-Robert Kolberg, Heggedal, Norway

[73] Assignee: A/S Nycotron, Drammen, Norway

[21] Appl. No.: 810,726

[22] Filed: Jun. 28, 1977

[51] Int. Cl.² .............................................. B01D 31/00
[52] U.S. Cl. .................................... 210/85; 210/321 B
[58] Field of Search ...................... 210/22, 321 K, 259, 210/85; 128/214 R, DIG. 13

[56] References Cited

U.S. PATENT DOCUMENTS

| 3,228,397 | 1/1966 | Moss | 128/DIG. 13 |
| 3,669,880 | 6/1972 | Marantz et al. | 210/22 |
| 4,024,059 | 5/1977 | Sausse | 210/259 X |

FOREIGN PATENT DOCUMENTS 2552304  5/1977  Fed. Rep. of Germany ....... 210/321 B Primary Examiner—Frank A. Spear, Jr.

Attorney, Agent, or Firm—Watson, Cole, Grindle & Watson

[57] ABSTRACT

A flow circuit for recirculating dialyzing liquid through a blood dialyzer includes an airtight bag sealed to conduits for liquid flow between the dialyzer and the bag which is enclosed in a closed container. The container is associated with scale means for weighing the liquid content of the bag and thus indicating the amount of ultrafiltrate extracted from the dialyzed blood and received by the dialyzing liquid. Further, the volume of the container outside the bag is connected with a suction pump operatively disposed to provide suitably reduced pressure within the bag and thus the complete recirculation circuit, with the purpose of achieving predetermined regulation of the extracted amount of ultrafiltrate. The bag and the associated flow conduits may be made of inexpensive plastic materials, which may be discarded after single usage. Thus, sterilization will be superfluous and uninhibited bacterial growth in the recirculation system will be avoided.

4 Claims, 1 Drawing Figure

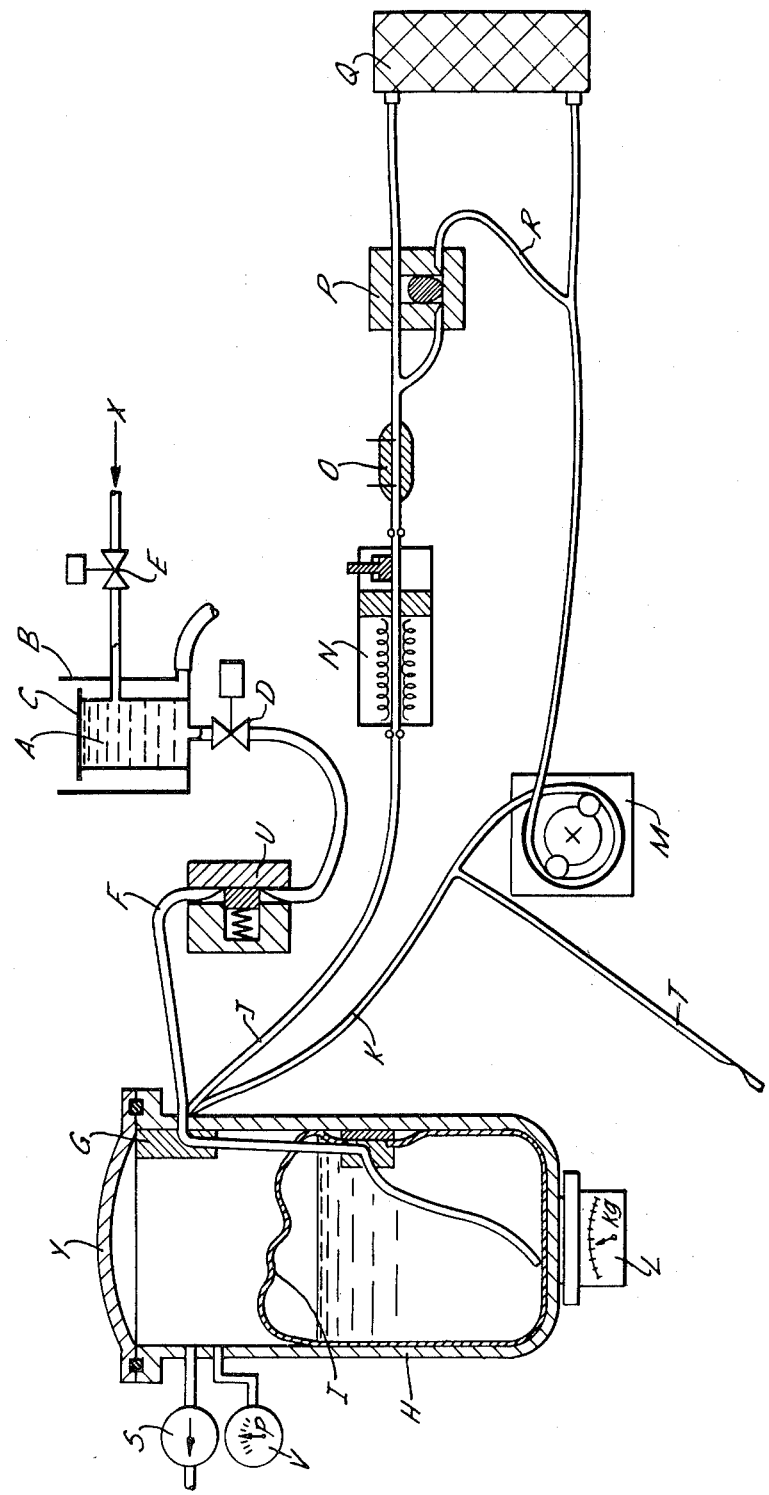

MEANS FOR REGULATING AND MONITORING DIALYSIS OF BLOOD IN A DIALYZER

This invention relates to a means for regulating and monitoring the dialysis of blood in a dialyzer, serving as an artificial kidney, in particular in connection with treatment of patients with chonic kidney deficiency.

Several embodiments of apparatus for this purposed exist, some of which are based upon recirculation of the dialyzing liquid through the dialyzer (artificial kidney). The liquid recirculating in this type of apparatus should preferably be sufficient to accomplish a complete dialysis of the blood of one patient without requiring replenishment during treatment. Some of the apparatus of this type have filtering and reconditioning means integral with the recirculation circuit, in order to reduce the required volume of liquid. A significant advantage of dialysis apparatus incorporating recirculating liquid as compared with apparatus which discharge the liquid upon a single passage through the dialyzer, is that the recirculating liquid allows suitable regulation and continuous monitoring of a most important parameter in connection with treatment of patients with kidney deficiency, namely the amount of liquid, the so-called ultra-filtrate, which is removed from the blood of the patient together with the poisonous substances during the dialysis. This monitoring may for example be done by continuous removal of excess liquid from the recirculating volume of liquid, this excess liquid being a direct measure of the amount of ultrafiltrate which has been extracted from the blood.

Alternatively, the recirculating liquid may be weighed as an indication of the amount of ultrafiltrate which has been extracted from the blood of the patient. By this method no excess liquid has to be removed from the recirculation circuit, which thus will constitute a real closed system and all contamination problems in connection with the extracted bacteria-containing excess liquid may be avoided. Furthermore, an electrical control signal may be more readily obtained from a weighing device than from volume measuring means.

The advantages achieved by recirculating the dialyzing liquid are, however, accompanied by a significant drawback. In known apparatus of this kind it has proved to be practically impossible to prevent unhampered bacterial growth. Chemical means or hot water may be employed for required disinfection, possibly in combination, or even internal autoclave sterilization of the liquid conducting part of the apparatus. Due to the large effective volumes involved, however, none of these methods are practical with regard to achieving satisfactory results in a complete recirculation circuit, and may easily leave bacterial growth which may defy control. On this background of prior art it is an object of the present invention to provide improved means for regulating and monitoring the blood dialyzing process in a dialyzer in a manner which secures an accurate measure and regulation of the amount of ultrafiltrate actually extracted from the blood.

In addition it is a further object of the invention to assure that the bacterial growth is avoided in order to eliminate all possibilities for medical complications for the patient undergoing dialysis treatment, as well as to protect the personnel operating the dialysis apparatus against infection.

Thus the invention concerns means for regulating and monitoring the dialysis of blood in a dialyzer included in a recirculation circuit for dialyzing liquid, the circuit furthermore comprising a closed liquid container as well as conduits for liquid flow between the dialyzer and the container, and the closed container being associated with scale means for weighing the content of the container and thereby indicating the amount of ultrafiltrate which has been extracted from the dialyzed blood and received by the dialyzing liquid.

On this basis the indicated objects of the invention are achieved by the features that the liquid in the closed container is enclosed within a tight bag, which is tightly sealed to the conduits, and the container volume outside the bag is connected with a suction pump for providing suitably reduced pressure in the recirculation circuit, with the purpose of achieving predetermined regulation of the extracted amount of ultrafiltrate.

The complete reciculation circuit will thus take the form of a closed system, possibly embodied in inexpensive materials, which may be discarded after single usage. Sterilization will be superfluous and uninhibited bacterial growth will be avoided.

Furthermore, the extracted amount of ultrafiltrate may readily be monitored by observing the indicated weight of the closed liquid container, and manually or automatically regulated by means of the aforementioned suction pump providing the desired reduced pressure in the container.

For further illustration of the means according to the present invention a preferred embodiment will now be described, with reference to the accompanying single drawing, which schematically shows a dialyzer apparatus equipped with means according to the present invention.

The drawing shows a dialyzer apparatus which comprises a dialyzer Q and a closed liquid container H as the main components of a recirculation circuit. The rest of this circuit primarily includes conduits J and K in the form of plastic tubing between the dialyzer and the container. The tubing guides the liquid through a temperature regulator N, a device O for measuring the concentration of dialyzing liquid, valve means P which may allow the liquid flow through a bypass R, and a circulation pump M. Inside the container H the dialyzing liquid is contained within a plastic bag I, which is tightly sealed to tubing K and J to form a closed circulation system. The bag I is also tightly connected with a conduit F which may supply liquid from an overflow tank B equipped with an internal container A for dialyzing concentrate, which in turn is supplied with tap water through valve E.

The liquid container H has a lid Y with an airtight fit, and is dimensioned to leave an air filled space above the liquid filled bag and with about the same volume as the bag. This air filled space communicates with outside air through a suction pump S mounted above the level of the liquid in the bag, with a gauge V indicating the air pressure in the container around the bag. The container H rests on suitable scales L for indicating any change in the weight of the content of the container.

The apparatus functions in the following manner:

Before the pump M is started the required amount of dialyzing concentrate is poured into the container A, until it overflows into the tank B, whereupon the lid C is put in place. Valves D and E are opened, allowing tap water to flow from the supply X through container A and, upon mixing with the concentrate, to proceed through the conduit F and a welding unit U to the plastic bag I, passing the inlet G of the container H. The conduit F is also tightly welded to the bag I, which is placed in the container H in advance. The weight of the inflow of liquid is registered by the scales L, which may be designed to cut off the water supply automatically when a predetermined amount of liquid is present in the container H (in the bag I). When the circulation pump M, which may be of the peristaltic type, is started, the dialyzing liquid will flow through the tubing J, the temperature regulator N, and the concentration gauge O (conductivity cell), to the valve P. According to the position of the valve, the liquid will flow either through the dialyzer O or through the bypass R, and further on to the pump M, which returns the liquid to the container H via tubing K.

By means of the suction pump S the entire recirculation circuit may be subject to reduced pressure, in order to enable a regulated removal of ultrafiltrate from the blood supplied to the dialyzer Q for treatment. The weight of the liquid contained in the main container H will then increase accordingly. This weight increase will be indicated by the scales L, and may be continuously monitored by an operator, to be maintained at a desired rate by regulation of the internal pressure in container H by means of the suction pump S. This pressure may be read on the gauge V and adjusted in order to obtain a suitable ultrafiltration rate for the patient being treated. The amount of ultrafiltrate actually removed may be read on the scales L at any time.

Alternatively, the pressure in the container may be automatically adjusted depending on the weight value sensed by the scales L by means of control means known in the art and connecting the scales L with the suction pump S.

Any leakage of air, for example into the dialyzer Q, or gases liberated from the water due to the reduced pressure, will accumulate above the liquid surface in the bag I, but will have no appreciable influence on the indicated weight of the ultrafiltrate. Upon termination of the dialysis, the tubing T is opened to remove the liquid from the circulation circuit with pump M running. When the circuit is empty, the lid of the container H is opened and the bag I removed to be discarded together with tubing F, J and K after their disconnection from the dialyzer Q and other circuit components.

The welding unit U serves to permanently close off tubing F after supply of the prescribed amount of dialyzing liquid to the liquid container H. In this way contamination of the liquid supply system during the dialyzing process is prevented.

I claim:

1. Means for regulating and monitoring the dialysis of blood in a dialyzer included in a recirculation circuit for dialyzing liquid, said circuit further comprising:
    (a) a liquid reservoir constituted by a flexible liquid tight bag;
    (b) conduits tightly sealed to said liquid tight bag for liquid flow in closed circuit between said bag and the dialyzer;
    (c) scale means for weighing the liquid contained in said bag, thereby indicating the amount of ultrafiltrate extracted from the dialyzed blood and received by the dialyzing liquid; and
    (d) a tightly closable pressure tank enclosing the liquid tight bag, the tank volume outside the bag being connected with a suction pump adapted to provide a suitably reduced pressure in said recirculation circuit, in order to achieving predetermined regulation of said extracted amount of ultrafiltrate from the blood.

2. Means according to claim 1, wherein said bag is a plastic bag, and said conduits for liquid flow are plastic tubings welded to the plastic bag.

3. Means according to claim 1, wherein said pressure tank is provided with a lid which may be opened for inserting said bag, when empty, into said tank, said bag furthermore being tightly connected with an inlet conduit for supplying liquid to the bag after its insertion.

4. Means according to claim 3, wherein said inlet conduit passes through a welding unit disposed and operatively adapted to sealingly close the inlet conduit after the supply of a prescribed amount of dialyzing liquid to said pressure tank.

* * * * *